(12) United States Patent
Håkansson et al.

(10) Patent No.: US 12,179,059 B2
(45) Date of Patent: Dec. 31, 2024

(54) SYSTEM AND METHOD FOR MONITORING ACTIVITY IN A GYM ENVIRONMENT

(71) Applicant: Sony Group Corporation, Tokyo (JP)

(72) Inventors: Jakob Håkansson, Basingstoke (GB); Axel Mulder, Basingstoke (GB)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 17/571,122

(22) Filed: Jan. 7, 2022

(65) Prior Publication Data

US 2022/0280837 A1 Sep. 8, 2022

(30) Foreign Application Priority Data

Mar. 5, 2021 (SE) .................................. 2150257-0

(51) Int. Cl.
| | |
|---|---|
| A63B 24/00 | (2006.01) |
| A63B 71/06 | (2006.01) |
| G06T 7/20 | (2017.01) |
| G06T 7/70 | (2017.01) |
| G06V 20/40 | (2022.01) |
| G06V 20/52 | (2022.01) |
| G06V 40/10 | (2022.01) |

(Continued)

(52) U.S. Cl.
CPC ...... *A63B 24/0062* (2013.01); *A63B 71/0622* (2013.01); *G06T 7/20* (2013.01); *G06T 7/70* (2017.01); *G06V 20/46* (2022.01); *G06V 20/52* (2022.01); *G06V 40/10* (2022.01); *G06V 40/23* (2022.01); *H04B 5/70* (2024.01); *H04N 7/18* (2013.01); *H04N 23/90* (2023.01); *A63B 2220/05* (2013.01); *A63B 2220/806* (2013.01); *A63B 2225/54* (2013.01); *G06T 2207/10016* (2013.01); *G06T 2207/30196* (2013.01); *G06T 2207/30221* (2013.01); *G06T 2207/30232* (2013.01)

(58) Field of Classification Search
None
See application file for complete search history.

(56) References Cited

U.S. PATENT DOCUMENTS 10,839,203 B1 * 11/2020 Guigues ............... G06V 10/774
10,905,916 B1    2/2021 Malik
(Continued)

OTHER PUBLICATIONS

Office Action and Search Report from corresponding Swedish Application No. 2150257-0, mailed on Jul. 22, 2021, 7 pages.
(Continued)

*Primary Examiner* — James M Anderson, II
(74) *Attorney, Agent, or Firm* — Tucker Ellis LLP (57) ABSTRACT

A system for monitoring activity in a gym environment includes a monitoring system configured to identify human representations in the gym environment and track movement of the human representations; a transceiver unit for receiving communication signals within the gym environment; a waypoint transmitter arranged at a predetermined location in the gym environment and configured to transmit a near field wireless signal; a control system configured to assign a specific human representation to an electronic device, responsive to the monitoring system detecting presence of the specific human representation at said location at a point in time associated with reception in the electronic device of the near field wireless signal.

17 Claims, 5 Drawing Sheets

(51) Int. Cl.
*G06V 40/20* (2022.01)
*H04B 5/70* (2024.01)
*H04N 7/18* (2006.01)
*H04N 23/90* (2023.01)

(56) References Cited

U.S. PATENT DOCUMENTS

| | | | |
|---|---|---|---|
| 2008/0170123 A1* | 7/2008 | Albertson | G06T 7/20 |
| | | | 348/157 |
| 2014/0270375 A1* | 9/2014 | Canavan | A61B 5/7246 |
| | | | 382/103 |
| 2016/0346617 A1 | 12/2016 | Srugo et al. | |
| 2017/0056726 A1 | 3/2017 | Dalebout et al. | |
| 2017/0173392 A1* | 6/2017 | Orfield | A63B 21/0628 |
| 2020/0034677 A1 | 1/2020 | Bengtsson et al. | |
| 2020/0342975 A1 | 10/2020 | Bengtsson et al. | |
| 2021/0205660 A1* | 7/2021 | Shavit | A63B 21/16 |
| 2022/0022748 A1* | 1/2022 | Al-Ali | A61B 5/021 |

OTHER PUBLICATIONS

Anonymous: "Radio-frequency identification—Wikipedia", Mar. 2, 2021 (Mar. 2, 2021), pp. 1-23, XP093086316, Retrieved from the Internet: [retrieved on Sep. 27, 2023].

* cited by examiner

| VIEW# | OBJECT# | KEYPOINT LOC |
|---|---|---|
| 1 | 1 | L1, L2, ..., L14 |
| 1 | 2 | L1, L2, ..., L14 |
| 1 | 3 | L1, L2, ..., L14 |
| 2 | 1 | L1, L2, ..., L14 |
| 2 | 2 | L1, L2, ..., L14 |
| 2 | 3 | L1, L2, ..., L14 |
| 3 | 1 | L1, L2, ..., L14 |
| 3 | 2 | L1, L2, ..., L14 |
| 3 | 3 | L1, L2, ..., L14 |

← ODD

SYSTEM AND METHOD FOR MONITORING ACTIVITY IN A GYM ENVIRONMENT

CROSS REFERENCE TO RELATED APPLICATIONS

The present application claims priority to Swedish patent application 2150257-0 filed on Mar. 5, 2021, the content of which is incorporated herein by reference in its entirety.

TECHNICAL FIELD

The invention relates generally to systems and methods for monitoring activity in a gym environment, for the purpose of detecting and logging a physical exercise. Specifically, the invention relates to a solution for ensuring proper allocation of detected activity to the person carrying out the exercise.

BACKGROUND

In recent years, there has been a virtual explosion in the popularity of exercise and physical fitness. There are many popular forms of physical exercise including, for example, running, bicycling, and weight training. The growing interest in weight training is reflected by the growing number of gyms found in both public and private settings.

One important aspect of any type of exercise program is the ability to track personal performance and progress. For example, people engaged in endurance or distance forms of exercise (e.g., running, swimming, bicycling, etc.) often track the distance and/or time associated with a particular run, swim, ride, etc. Similarly, people using cardiovascular exercise machines (e.g., treadmills, stair-steppers, stationary bicycles, etc.) are often interested in knowing how long they exercise or how many calories they burn during a particular session. For weightlifting exercises, both weight and repetition are important features to log.

There is a strong digitization trend in the gym industry. Various systems have been suggested for monitoring exercise activity in a gym environment. Several vendors are building machines with inbuilt reps and weight measurement. Such exercise machines are generally expensive, with built-in displays, and require AC power.

One way of accomplishing tracking of an exercise is to adapt a tool used in the exercise, such as a weight machine, with a tracking system. One example of such a system was disclosed in WO2019/147174A1. That disclosure describes a monitoring system for monitoring exercise machines comprising a lifting mechanism for selectively engaging one or more of the weights. The exercise machines comprise a plurality of stacked weights, and a monitoring system comprises, for each of the exercise machines, a repetition detector and an exercise machine identifier. The monitoring system further comprises an observer and a user device.

A drawback with this type of systems is that they are not appropriate for tracking an exercise activity that is not carried out using a specific tool or machine. Accordingly, there still exists a need for improvement in the art of systems and methods for monitoring activity in a gym environment.

SUMMARY

It is an objective to at least partly overcome one or more limitations of the prior art. Specifically, it is an object to provide a solution for tracking exercise data appropriately linked to an electronic device, which may be associated with a person or an account.

One or more of these objectives, as well as further objectives that may appear from the description below, are at least partly achieved by a system and a method according to the independent claims, embodiments thereof being defined by the dependent claims.

According to one aspect, the proposed solution relates to a system for monitoring activity in a gym environment, wherein the system comprises:
 a monitoring system configured to identify human representations in the gym environment and track movement of the human representations;
 a transceiver unit for receiving communication signals within the gym environment;
 a waypoint transmitter arranged at a predetermined location in the gym environment and configured to transmit a near field wireless signal;
 a control system configured to assign a specific human representation to an electronic device, responsive to the monitoring system detecting presence of the specific human representation at said location at a point in time associated with reception in the electronic device of the near field wireless signal.

BRIEF DESCRIPTION OF THE DRAWINGS

Embodiments will now be described in more detail with reference to the accompanying schematic drawings.

DETAILED DESCRIPTION

Embodiments will now be described more fully hereinafter with reference to the accompanying drawings, in which some, but not all, embodiments are shown. Indeed, the subject of the present disclosure may be embodied in many different forms and should not be construed as limited to the embodiments set forth herein; rather, these embodiments are provided so that this disclosure may satisfy applicable legal requirements.

Also, it will be understood that, where possible, any of the advantages, features, functions, devices, and/or operational aspects of any of the embodiments described and/or contemplated herein may be included in any of the other embodiments described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, the terms "multiple", "plural" and "plurality" are intended to imply provision of two or more items, whereas the term a "set" of items is intended to imply a provision of one or more items. The term "and/or" includes any and all combinations of one or more of the associated listed items. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments. The term "compute", and derivatives thereof, is used in its conventional meaning and may be seen to involve performing a calculation involving one or more mathematical operations to produce a result, for example by use of a computer.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present disclosure. Well-known functions or constructions may not be described in detail for brevity and/or clarity. Unless otherwise defined, all terms (including technical and scientific terms) used herein have the same meaning as commonly understood by one of ordinary skill in the art to which this disclosure belongs. Like numbers refer to like elements throughout.

Figure 1:
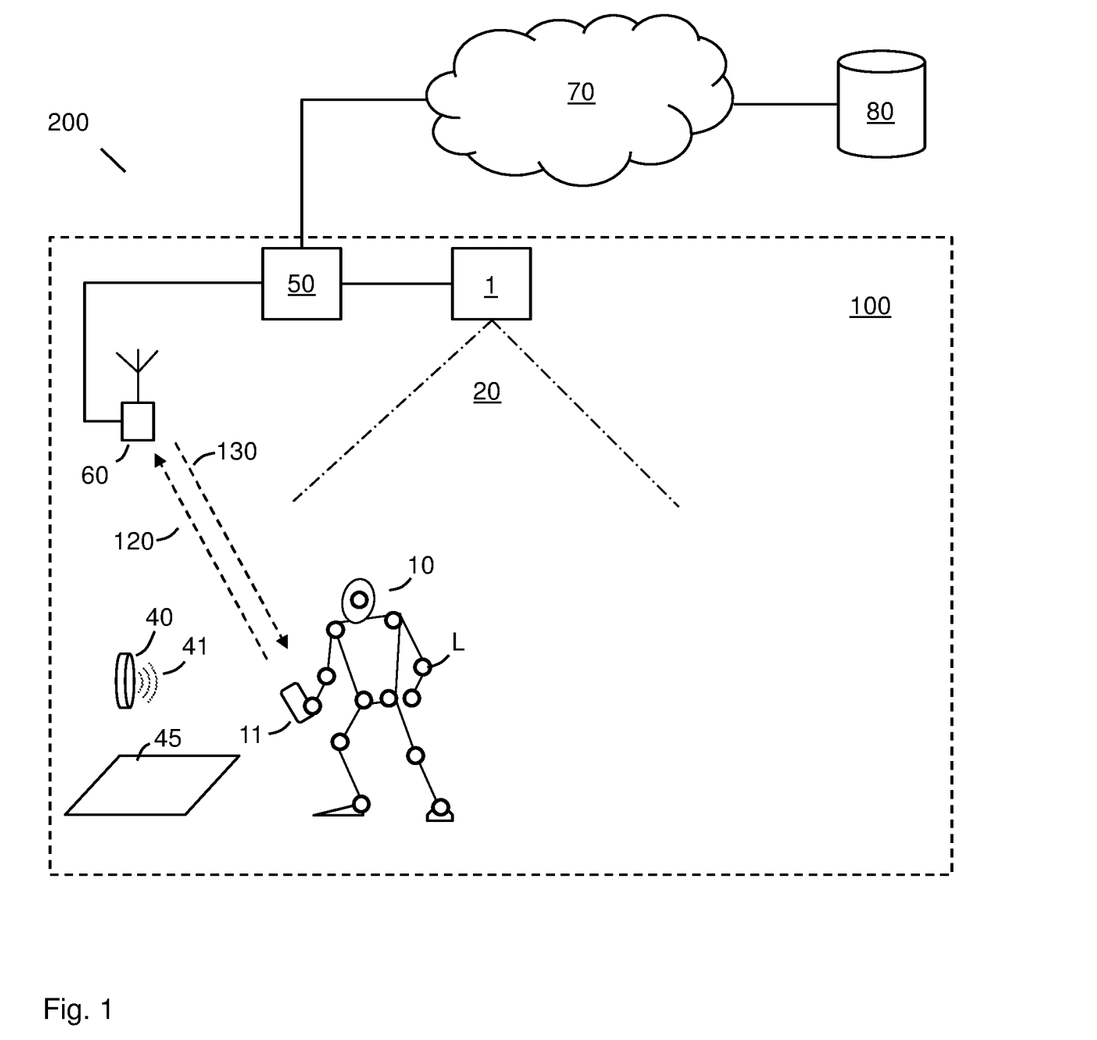
FIG. 1 illustrates an embodiment of a system according to the proposed solution, configured to monitor and track exercise activity in a gym environment.

FIG. 1 schematically illustrates a context of the proposed solution, and various features and elements forming part of a system 200 configured to operate in accordance with the proposed solution.

The proposed solution is based on the concept of employing a monitoring system 1 to monitor a gym environment 100, and to identify human representations in the gym environment and track movement of the human representations. The gym environment 100 may be a room, a series of rooms, a part of a room, or an outdoor area.

In the drawing, a person 10 is present in the gym environment 100. The monitoring system 1 is configured to detect presence of objects in the gym environment 100, and to identify an object as a human. As will be described in further detail below, the monitoring system 1 may comprise one or more imaging devices, such as video cameras, arranged to capture image data of one or more views of the gym environment 100. By image detection and processing of the captured image data, various key points L of detected objects may be identified. Based on e.g. shape, size, correlated movement of key points, and other recognizable patterns, a detected object may be characterized as a human person. The combined key points of an object detected and characterized as a human person is referred to herein as a human representation O1.

The system comprises a control system 50, identified in the drawing as a single element for the sake of simplicity. It should be noted, though, that the control system 50 may completely or partly share resources with the monitoring system 1. Alternatively, or additionally, the control system 50 may employed shared logic in a cloud arrangement.

The system further comprises a transceiver unit 60 for receiving communication signals 120 within the gym environment 100, and optionally for transmitting 130 communication signals. The transceiver unit 60 may be configured to operate according to a protocol capable of receiving radio signals within the entire gym environment 100. The transceiver unit 60 may e.g. be configured to operate as a cellular base station or as a wireless local area hotspot, e.g. a Wi-Fi hotspot under an IEEE 802.11 protocol, or by Bluetooth, or by any other wireless communication technology, either standardized or proprietary. The transceiver unit 60 may inter alia receive communication signals 120 from electronic device present in the gym environment 100, such as portable or wearable electronic devices. An example of such an electronic device is the portable electronic device 11, associated with and carried by the person 10. The transceiver unit 60 is communicatively connected to the control system 50.

The system further comprises a waypoint transmitter 40, arranged at a predetermined location 45 in the gym environment 100 and configured to transmit a near field wireless signal 41. The waypoint transmitter 40 may be configured such that the near field wireless signal 41, configured in accordance with a near field communication protocol, is only detectable at said predetermined location 45. The waypoint transmitter 40 may thus be configured for proximity communication, using e.g. RFID (Radio-frequency identification), NFC (Nearfield Communication), BLE (Bluetooth Low Energy) or other. The range of successful reception of a nearfield wireless signal 41 transmitted from the waypoint transmitter 40 may be less than a certain distance, such as 100 cm, 50 cm, 20 cm, 10 cm, 5 cm or less. In some embodiments the waypoint transmitter 40 is communicatively separated from the control system 50, the transceiver unit 60, and the monitoring system 1. In such embodiments, the waypoint transmitter 40 is configured to transmit its nearfield wireless signal 41 without being triggered from the control system 50. In some embodiments, the character, or conveyed content, of the nearfield wireless signal 41 may vary over time, in a pattern known to the control system 50. The simple implementation and operation of the waypoint transmitter 40 ensures that it may be embodied as a low complexity device with low energy consumption, which makes it suitable to be realized as a battery-charged nearfield wireless signal transmitter.

In some embodiments, the dimension of the predetermined location 45 correlates with the communication range of the waypoint transmitter 40. The predetermined location is detectable by the monitoring system 1, and may be configured to conveniently fit one person at a time. in various embodiments predetermined location 45 may be defined by a floor or ground area, or a 3D space, at the waypoint transmitter 40. In some embodiments, the location area 45 may be configured as a gated area, so as to conveniently only fit one person at a time. In some embodiments, the predetermined location area comprises a turnstile or a door, e.g. arranged for entering the gym environment 100.

The control system 50 is configured to assign a specific human representation to the electronic device 11, responsive to the monitoring system 1 detecting presence of the specific human representation O1 at the predetermined location 45 at a point in time associated with reception in the electronic device 11 of a near field wireless signal 41 from the waypoint transmitter 40.

In some embodiments, the near field wireless signal triggers the electronic device 11 to transmit a communication signal 120 to the transceiver unit 60, indicating reception in the electronic device 11 of the near field wireless signal 41. In some embodiments, an application client in the electronic device 11 may control the electronic device 11 to carry out said transmission 120 responsive to detecting the nearfield wireless signal 41. The application client may be in such an embodiment operate in conjunction with an application host in the control system 50.

In some embodiments, said point in time may be a time stamp associated with the transmission from the electronic device 11, or the reception in the transceiver unit 60, of the wireless communication signal 120. In other embodiments, said point in time may be a time stamp indicating the time of reception of the nearfield wireless signal 41 in the electronic device 11.

By means of the proposed solution, a detected human representation O1 may be linked to an electronic device 11, to ensure that exercise activity based on movement of the human representation O1, as tracked by the monitoring system 1 in the gym environment 100, can be appropriately associated with a person linked with the electronic device 11. The system design assures that persons not desiring to have their activity logged in the gym environment are not identified, which provides integrity to the system. Moreover, synchronization with the system 200 need only be executed once in the gym environment 100, without requiring that the person continues to wear or carry the electronic device during various forms of exercise activity in the gym environment 100. This assures user flexibility.

Before proceeding with description of additional features and functions of the system 22, a general presentation of the elements associated with the system 200 will be discussed.

The monitoring system 1 operates to recover 3D position and 3D pose of objects from images, such as iterative still images or a video stream. One solution known in the art is to use multiple cameras with overlapping fields of view 20, where the position and orientation of the cameras is known with reasonable accuracy, for example by measurement during installation. In operation, 3D positioning and pose determination typically comprises two stages: processing of individual video streams from the multiple cameras for detection of objects and key points of the respective object, and processing the detections to identify correspondence between detections of the same object in different views and calculating the position and/or pose of the respective object based on the correspondence between detections, and optionally temporal information. There are several established techniques for performing the first stage with good performance, for example by use of convolutional neural networks.

As used herein, "key point" has its conventional meaning in the field of computer vision and is also known as an interest point. A key point is a spatial location or point in an image that define what is interesting or what stand out in the image and may be defined to be invariant to image rotation, shrinkage, translation, distortion, etc. More generally, a key point may be denoted a "reference point" on an object to be detected in the image, with the reference point having a predefined placement on the object. Key points may be defined for a specific type of object, for example a human body, a part of the human body, or an inanimate object with a known structure or configuration. In the example of a human body, key points may identify one or more joints and/or extremities. Key points may be detected by use of any existing feature detection algorithm(s), for example image processing techniques that are operable to detect one or more of edges, corners, blobs, ridges, etc. in digital images. Non-limiting examples of feature detection algorithms comprise SIFT (Scale-Invariant Feature Transform), SURF (Speeded Up Robust Feature), FAST (Features from Accelerated Segment Test), SUSAN (Smallest Univalue Segment Assimilating Nucleus), Harris affine region detector, and ORB (Oriented FAST and Rotated BRIEF). Further information about conventional key point detectors is found in the article "Local invariant feature detectors: a survey", by Tuytelaars et al, published in Found. Trends. Comput. Graph. Vis. 3(3), 177-280 (2007). Further examples of feature detection algorithms are found in the articles "Simple Baselines for Human Pose Estimation and Tracking", by Xiao et al, published at ECCV 2018, and "Deep High-Resolution Representation Learning for Human Pose Estimation", by Sun et al, published at CVPR 2019. Correspondingly, objects may be detected in images by use of any existing object detection algorithm(s). Non-limiting examples include various machine learning-based approaches or deep learning-based approaches, such as Viola-Jones object detection framework, SIFT, HOG (Histogram of Oriented Gradients), Region Proposals (RCNN, Fast-RCNN, Faster-RCNN), SSD (Single Shot MultiBox Detector), You Only Look Once (YOLO, YOLO9000, YOLOv3), and RefineDet (Single-Shot Refinement Neural Network for Object Detection).

FIGS. 2A to 2D are enclosed to show one way of operating the monitoring system 1, usable in the proposed solution. The monitoring system 1 is configured for determining positioning of one or more objects in a scene based on a plurality of views of the scene, also known as a "multiview". The positioning may be 3D object positioning, which involves determining a single 3D position of a key point of the respective object in the scene, or 3D pose determination, which involves determining 3D positions of a plurality of key points of the respective object in the scene. The views may be digital images and may be produced by a fixed or non-fixed arrangement of imaging devices. The views represent different viewpoints onto the scene, or parts thereof, and the respective object is reproduced as a two-dimensional object in the respective view.

Figure 2A:
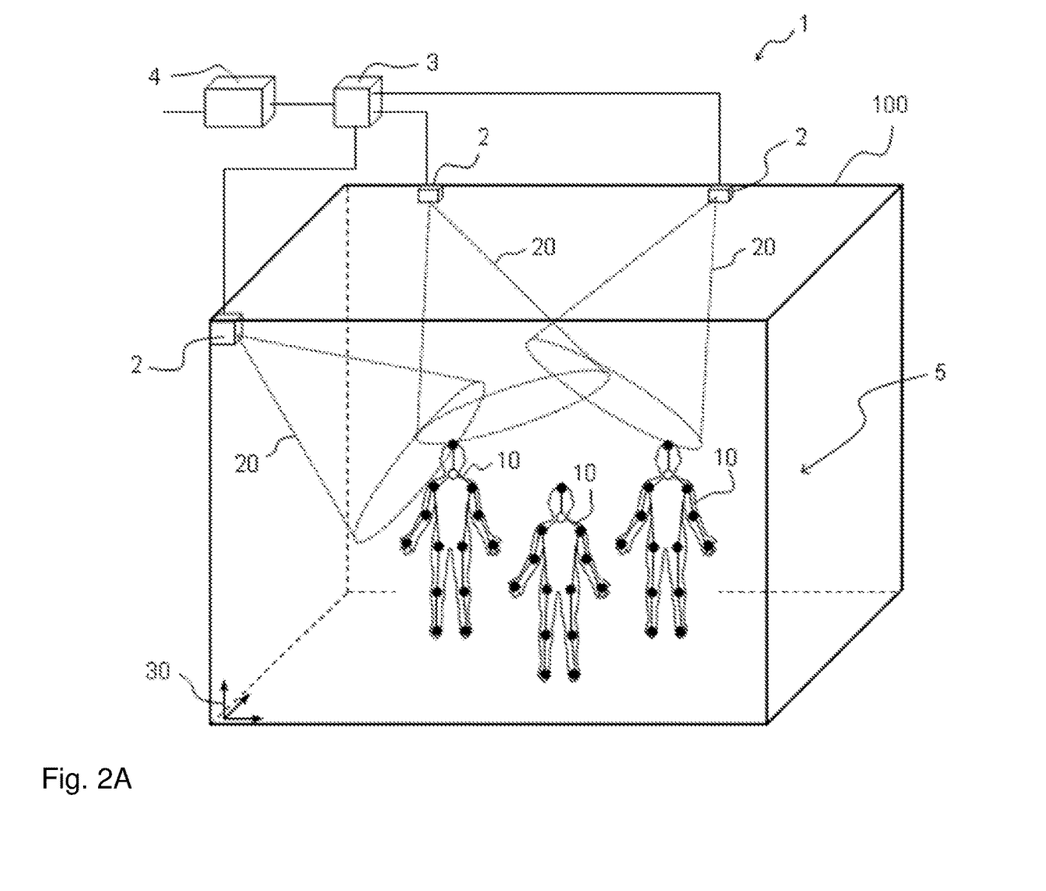
FIGS. 2A-2D illustrate various aspects of an example of a monitoring system for detecting a human representation in the gym environment, for use in the system of the proposed solution.

FIG. 2A shows an example arrangement of the monitoring system 1 in accordance with an embodiment. The monitoring system 1 is arranged to monitor a scene 5 of the gym environment 100. In the illustrated example, three individuals 10 are in the gym environment 100. The monitoring system 1 comprises a plurality of imaging devices 2, for example digital cameras, which are oriented with their respective field of view 20 towards the scene 5. The scene 5 is associated with a fixed 3D coordinate system 30 ("scene coordinate system"). The imaging devices 2 may be fixed or moveable, and their relative positions and orientations are known for each image taken. The imaging devices 2 may be synchronized to capture a respective image at approximately the same time, or at least with a maximum time difference which depends on the expected maximum speed of movement of the objects 10. In one example, a maximum time difference of 0.1-0.5 seconds may provide sufficient accuracy for normal human motion.

The images captured by the imaging devices 2 are received by a detection device 3, which is configured to determine one or more key points of one or more objects in the respective image. The detection device 3 may implement any conventional object detection technique for identifying objects of a generic or specific type in the respective image and may implement any conventional feature detection technique for identifying one or more key points of the respective object, for example any of the feature and object detection techniques mentioned hereinabove. The detection device may also pre-process the incoming images, for example for noise reduction, contrast enhancement, etc. In an alternative configuration, the monitoring system 1 comprises a plurality of detection devices 3, for example one for each imaging device 2, where the detection devices 3 may be co-located or integrated with the imaging devices 2.

Figure 2B:
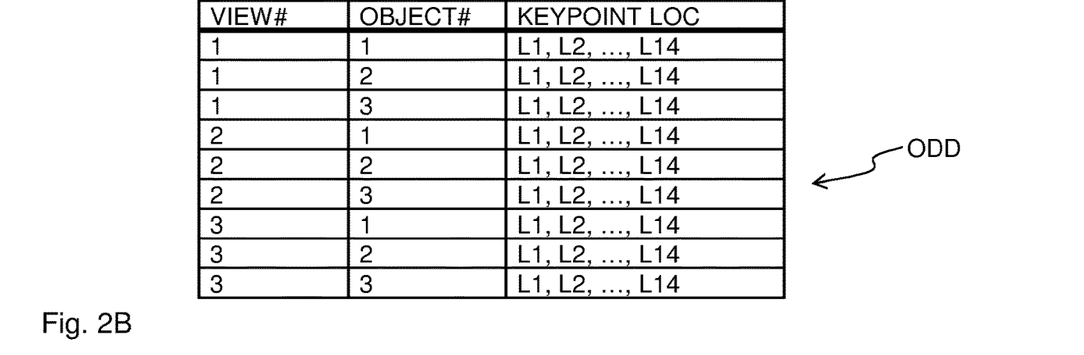
Figure 2C:
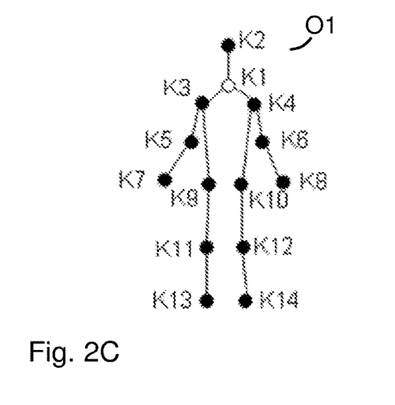
Figure 2D:
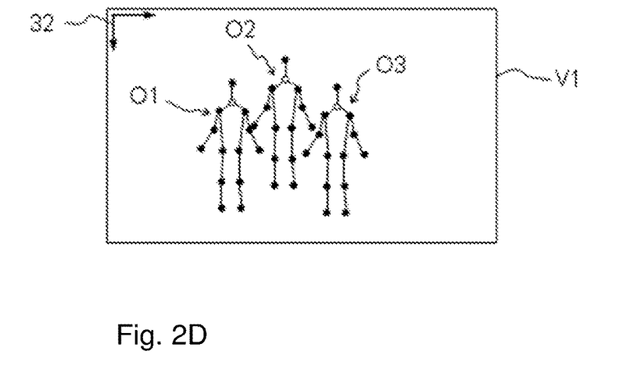

The detection device 3 produces object detection data, which identifies one or more key points of one or more objects detected in the respective image. The object detection data is denoted ODD in the following. An example of the ODD is shown in FIG. 2B. Although FIG. 2B illustrates a table, the ODD may be given in any format. In the illustrated example, the ODD represents each image (view) by a respective view identifier (1-3 in FIG. 2B) and each object by a respective object identifier (1-3 in FIG. 2B), and comprises a key point position for each key point detected for the respective object (L1-L14 in FIG. 2B). In the following, for clarity of presentation, object identifiers will be designated O1, O2, O3, etc., and view identifiers will be designated V1, V2, V3, etc. An example of key points K1-K14, forming a human representation O1 for a human individual 10, is shown in FIG. 2C. However, any number of key points may be detected depending on implementation. One or more of the key points may be designated as a main key point. The main key point may be identifiable with greater accuracy than other key points and/or may have a specific location within the object, for example close to its center. In the schematic example of FIG. 2C, the main key point K1 is indicated by an open circle and corresponds to the neck of the respective individual. The detection device 3 is configured to detect a predefined number of key points of the respective object. If a key point is not detected, the detection device 3 may enter a predefined value (for example, a null value) into the ODD. The detection device 3 may also include a confidence score for each object and/or key point in the ODD, the confidence score representing a level of certainty for the respective detection. FIG. 1D shows an example view V1 captured by one of the imaging devices 2 in FIG. 1A and represents three detected objects O1, O2 and O3 with associated key points. The detected position of the respective key point is given by 2D coordinates in a local and fixed coordinate system 32 of the view V1.

The system 1 further comprises a positioning device 4, which is configured to operate on the ODD to compute, and possibly track over time, one or more 3D positions of one or more objects in the scene 5. It may be noted that positioning device 4 may comprise a plurality of units, which may be co-located with respective detection devices, wherein calculating 3D positioning is distributed. For example, a first positioning device 4A and detection device 3A are co-located and configured to track a human representation O1, whilst a second positioning device 4B and detection device 3B are co-located and configured to track a human representation O2.

Based on the above, the monitoring system 1 thus operates logic configured to process video streams from the plurality of cameras 2 for detection of key points L of an object, and to associate said key points L to positions on a human body. The logic may be shared by the detection device 3 and the positioning device 4.

Figure 3:
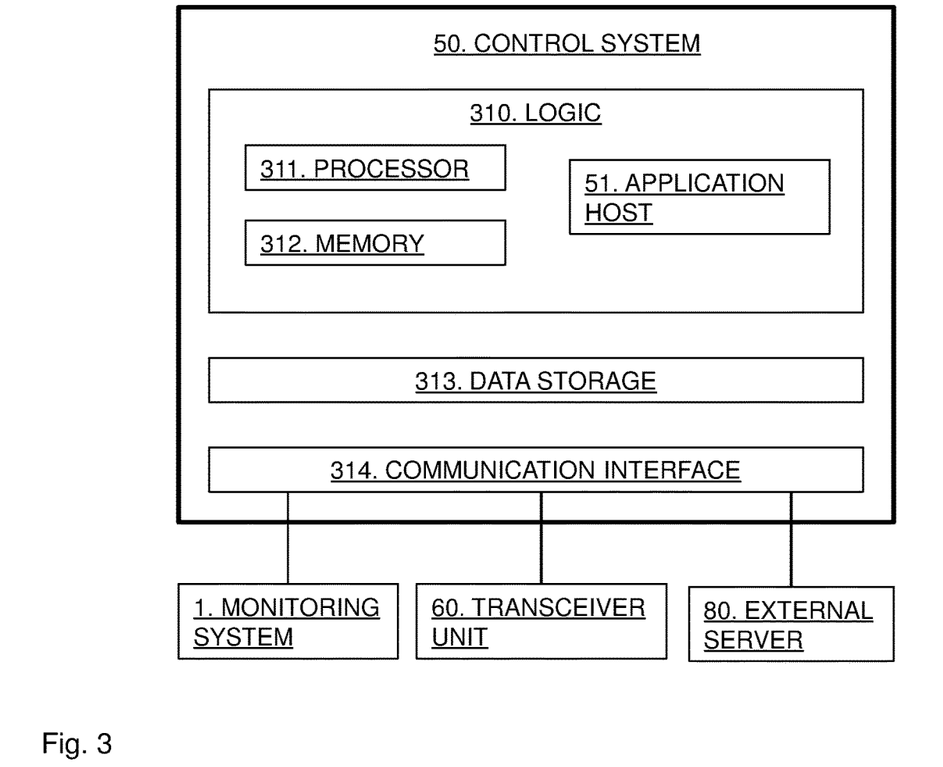
FIG. 3 schematically illustrates an example of a control system configured to control operation in the system of the proposed solution.

FIG. 3 schematically illustrates an example of the control system 50 for use in the system 200 as presented herein, and for carrying out the method steps as outlined.

The control system 50 comprises logic 310 configured to control the system 200, including to communicate with other elements of the system 200.

The logic 310 may include a processing device 311, including one or multiple processors, microprocessors, data processors, co-processors, and/or some other type of component that interprets and/or executes instructions and/or data. The processing device 311 may be implemented as hardware (e.g., a microprocessor, etc.) or a combination of hardware and software (e.g., a system-on-chip (SoC), an application-specific integrated circuit (ASIC), etc.). The processing device 311 may be configured to perform one or multiple operations based on an operating system and/or various applications or programs.

The logic 310 may further include memory storage 312, which may include one or multiple memories and/or one or multiple other types of storage mediums. For example, the memory storage 312 may include a random access memory (RAM), a dynamic random access memory (DRAM), a cache, a read only memory (ROM), a programmable read only memory (PROM), flash memory, and/or some other type of memory. The memory storage 312 may include a hard disk (e.g., a magnetic disk, an optical disk, a magneto-optic disk, a solid state disk, etc.).

The memory storage 312 is configured for holding computer program code, which may be executed by the processing device 311, wherein the logic 310 is configured to control the control system 50 to carry out any of the method steps as provided herein. Software defined by said computer program code may include an application or a program that provides a function and/or a process. The software may include device firmware, an operating system (OS), or a variety of applications that may execute in the logic 310.

The logic may be configured to hold and run an application host 51 of a software application for communicating with one or more application clients stored in electronic device. The application of the application host may be unique to the gym environment 100, or be associated with an operator of various gyms or other facilities. The application host 51 may further be used for securely communicating exercise data, as determined based on tracked movement, with the electronic device 11 or with an external server 80, holding a database or an account linked to the electronic device 11 or to a user associated with the electronic device.

The control system may optionally comprise data storage 313, for storing user account data and/or exercise data.

The control system 50 further comprises a communication interface 314, for communication with other elements of the system 200 or associated therewith. The communication interface may comprise a connection to the monitoring system 1, which may be wired or wireless. As noted, various elements of the monitoring system 1 may share resources with the control system 50, such as logic and/or memory. Further, the control system 50 is connected to the transceiver unit 60, for communication of wireless communication signals with inter alia electronic devices present in the gym environment. Further, the control system may comprise an interface for communicating with a remote server 80, as described.

It may be noted that detection and recognition of movement, and correlation of the detected movement with a certain exercise activity, is not outlined in detail herein as these are not features on which the proposed solution relies. However, it may be noted that based on detected key points and association thereof with various body parts or joints of a human representation, any movement of those key points may be mapped to one of a plurality of detectable motions, stored in the system 200. The detection and recognition of exercise activity, based on the movement detected by the monitoring system 1, may be carried out in the monitoring system 1 or in the control system 50, or remotely in the server 80.

Figure 4:
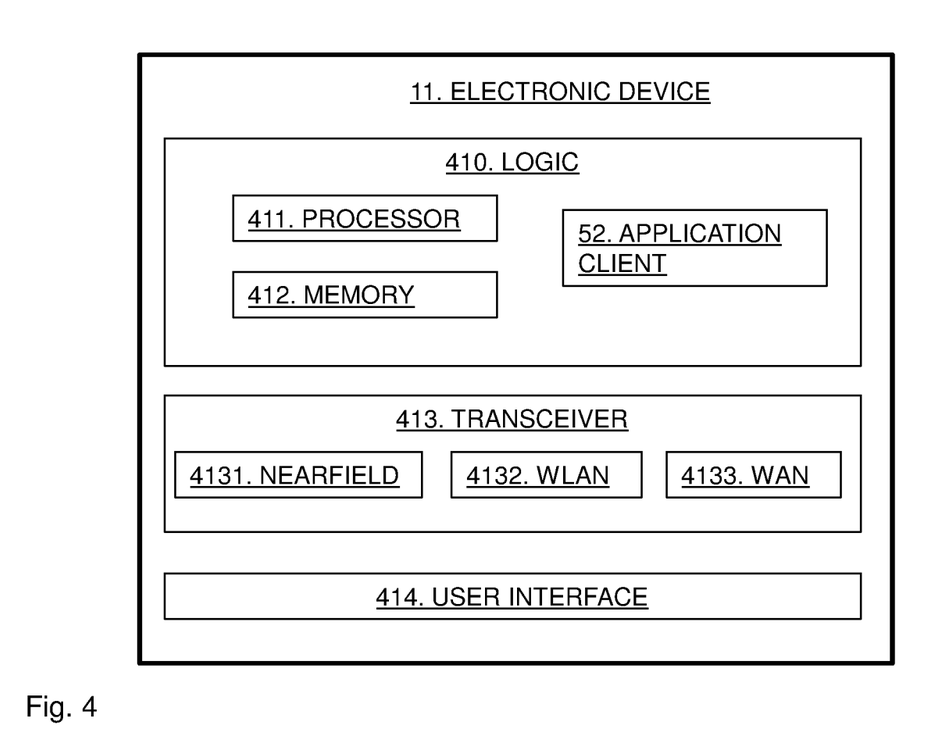
FIG. 4 schematically illustrates an example of an electronic device, configured to operate with the system of the proposed solution.

FIG. 4 schematically illustrates an embodiment of the electronic device 11. The electronic device 11 may be a radio communication terminal, such as a cellular device configured to operate in a wireless cellular network, e.g. a 5G New Radio network. Alternatively, the electronic device is only configured for non-cellular communication, e.g. wi-fi. As mentioned, the electronic device may optionally be a wearable device, such as a clip-on or a bracelet.

The electronic device 11 comprises logic 410 configured to control communication of data, via a transceiver 413. The logic 410 may include a processing device 411, including one or multiple processors, microprocessors, data processors, co-processors, and/or some other type of component that interprets and/or executes instructions and/or data. The processing device 411 may be implemented as hardware (e.g., a microprocessor, etc.) or a combination of hardware and software (e.g., a system-on-chip (SoC), an application-specific integrated circuit (ASIC), etc.). The processing device 411 may be configured to perform one or multiple operations based on an operating system and/or various applications or programs.

The logic 410 may further include memory storage 412, which may include one or multiple memories and/or one or multiple other types of storage media. For example, the memory storage 412 may include a random access memory (RAM), a dynamic random access memory (DRAM), a cache, a read only memory (ROM), a programmable read only memory (PROM), flash memory, and/or some other type of memory. The memory storage 412 may include a hard disk (e.g., a magnetic disk, an optical disk, a magneto-optic disk, a solid state disk, etc.).

The memory storage 412 is configured for holding computer program code, which may be executed by the processing device 411, wherein the logic 410 is configured to control the electronic device 11 to carry out any of the method steps as provided herein. Software defined by said computer program code may include an application or a program that provides a function and/or a process. The software may include device firmware, an operating system (OS), or a variety of applications that may execute in the logic 410.

The electronic device 11 further comprises a transceiver 413, which may comprise a plurality of different signal transceivers, such as radio transceivers, for communicating with various entities of the system 200 and possibly with a radio communication network. The transceiver 413 may thus include a radio receiver and transmitter for communicating through at least an air interface. As an example, the electronic device 11 may comprise one or more of a transceiver 4131 for receiving a nearfield wireless signal, e.g. using NFC, BLE, RFID or similar. The nearfield transceiver 4131 is configured for receiving a nearfield wireless signal from waypoint transmitters 40 of the system 200. The transceiver 413 may further comprise a wireless local area network (WLAN) transceiver 4132, for communication with the transceiver unit 60 of the system 60. The transceiver may further comprise a wide area network (WAN) transceiver 4133, e.g. for communication in a cellular network.

The logic 410 may be configured to hold and run an application client 52 of a software application for communicating with the application host 51 stored in control system 50. The application client 52 may inter alia be configured to control the electronic device 11 to transmit a wireless communication signal, using transceiver 4132 or 4133, to the transceiver unit 60 of the system 200, responsive to detecting a nearfield wireless signal from a waypoint transmitter 40. The application host may also be configured to convey an identification of the electronic device, in communication with the system 200.

The electronic device 11 may further comprise a user interface, such as a display and/or an audio output, for allowing a person 10 using the electronic device to properly operate the device in accordance various embodiments of the proposed solution.

The electronic device 11 may e.g. be a mobile communication device such as a mobile phone, a wearable device such as a bracelet or a clip-on device, or even a device embedded into a garment or shoe of the human 10. The electronic device may further comprise distributed elements, which are communicatively linked. The electronic device 11 may thus comprise a first member comprising a nearfield receiver 4131, configured to receive a nearfield wireless signal from the waypoint transmitter 40, and a second member comprising a wireless transceiver 4132 and/or 4133 capable of transmitting communication signals to the transceiver unit 60. In this context, the first and second members may communicate with each other by wired or wireless communication.

Successful operation of the proposed method relies on the notion that interaction between the system 200 and the electronic device 11 is only possible if the person carrying the electronic device 11 has physically moved to the waypoint transmitter 40. In that scenario, the system 200 can detect the closest human representation, such as the human representation detected in the predetermined location area 45 of the waypoint transmitter 40, and with high certainty assign the human representation to the user associated with the electronic device 11, such as by a user account associated with the system 22. The signal 120 transmitted to the system 200 operates a request for tracking, and for storing exercise data connected to the user account of the electronic device 11. Upon transmission 120 of that request, and successful detection of a human representation O1 at the predetermined location area 45, the application host in the control system 50 may be configured to provide feedback to the person 10 carrying the electronic device 11, e.g. in the form of visuals and/or vibrations, verifying the user of the electronic device 11 that the connection has been made and the tracking is ongoing. This may be carried out by transmitting a feedback signal 130 to the electronic device 11, for output using the user interface 414 of the electronic device 11, under control of the application client 52. Alternatively, the feedback may be provided by an output interface of the system 200, e.g. arranged at the predetermined location 45 (not shown).

In some embodiments, the control system 50 is configured to store exercise activity data associated with said electronic device, based on movement detected by the monitoring system 1 of the assigned specific human representation O1. Storing may be executed by transmitting the exercise activity data to a server 80 associated with a user account linked to the electronic device 11, either arranged locally in the control system 50 or remotely connected through a communications network, such as the Internet. The server 80 may be accessed by the person 10 by means of user verification according to state of the art procedures. Alternatively, the control system 50 may be configured to store the exercise data temporarily in a local memory 313, and transmitting the exercise data to the electronic device 11, e.g. by the transceiver unit 60.

In some embodiments, a limit may be defined for how close to the waypoint transmitter 40 a human representation needs to be located in order for a request for tracking to be successful. This limit may in some embodiments define the predetermined location area, and may e.g. be a certain distance counted from the waypoint transmitter 40. In case a request for tracking is transmitted from an electronic device 11 but the person whose human representation is nearest the waypoint transmitter moves away quickly, or there is more than one human representation detected by the monitoring system 1 at the predetermined location 45, the request is rejected. This, too, may be indicated by a feedback signal, similar to what was outlined for a successful connection. A new attempt to trigger a request for tracking may then be carried out by the person 10, by again approaching the waypoint transmitter 40 with the electronic device 11, and thereby triggering a new request for tracking 120.

In some embodiments, the system 200 is configured with a mechanism for ensuring proper linking of a human representation O1 to an electronic device 11, and in extension to link tracked exercise activity of a human representation O1 to an account or database associated with the electronic device 11, or a user of the electronic device 11. This mechanism entails that the system 200 is configured to output a message indicating a test motion, wherein the control system 50 is configured to assign the specific human representation O1 to the electronic device 11, e.g. the electronic device 11 from which the request for tracking 120 was received, based on the monitoring system 1 detecting a movement of the specific human representation O1 corresponding to said test motion.

The test motion is typically a movement which is easily identifiable by the monitoring system 1. Examples of such a test motion may comprise a movement in a certain direction or with a certain indicated body part, e.g. a wave or stretch of a hand or arm, a squat, a bend of the body, or any other motion that the monitoring system 1 can detect.

In one embodiment, the control system 50 is configured to control the transceiver unit 60 to transmit said message to the electronic device 11, for output on the user interface 414 on the electronic device 11, under control of the application client. This may e.g. comprise a video clip or animation of the test motion, or an audible description. In an alternative embodiment, the control system 50 is configured to output said message on an interface arranged at said location (not shown).

In some embodiments, the control system 50 is configured to request a test motion to be carried out based on a rejected request for tracking 120. Alternatively, the test motion is mandatory for successfully obtaining tracking. The control system 50 may nevertheless be configured to assign a specific human representation O1 to the electronic device 11 based on the monitoring system 1 detecting the movement corresponding to said test motion within a predetermined time period, such as within 3 s 5 s or 10 s from transmitting or outputting the message conveying test motion.

In some embodiments, the test motion is randomly selected from a group of test motions. This way, if a number of human representations are detected one after another at the predetermined location 45, such as at an entry to the gym environment 100, proper connection of an electronic device to the person carrying it, by distinguishing between different motions.

In some embodiments, the system 200 is further aided in the proper association of a human representation to an electronic device 11 by being configured to determine a physical characteristic of the specific human representation, such as height or build, and to assign the human characteristic to said electronic device 11 based on the determined physical characteristic matching prestored characteristic data associated with said electronic device. The determination of a physical characteristic may be carried out based on image data collected by the monitoring system 1, and may further comprise image analysis based on markers at the location area, e.g. indicating levels of height.

When a request for tracking 120 is successfully processed in the control system 50, thereby assigning a human representation O1 to the electronic device 11, the control system 50 may be configured to control the transceiver unit 60 to transmit an acknowledgment signal to the electronic device 11, in which the acknowledgment may e.g. be output audibly and/or by vibration.

Figure 5:
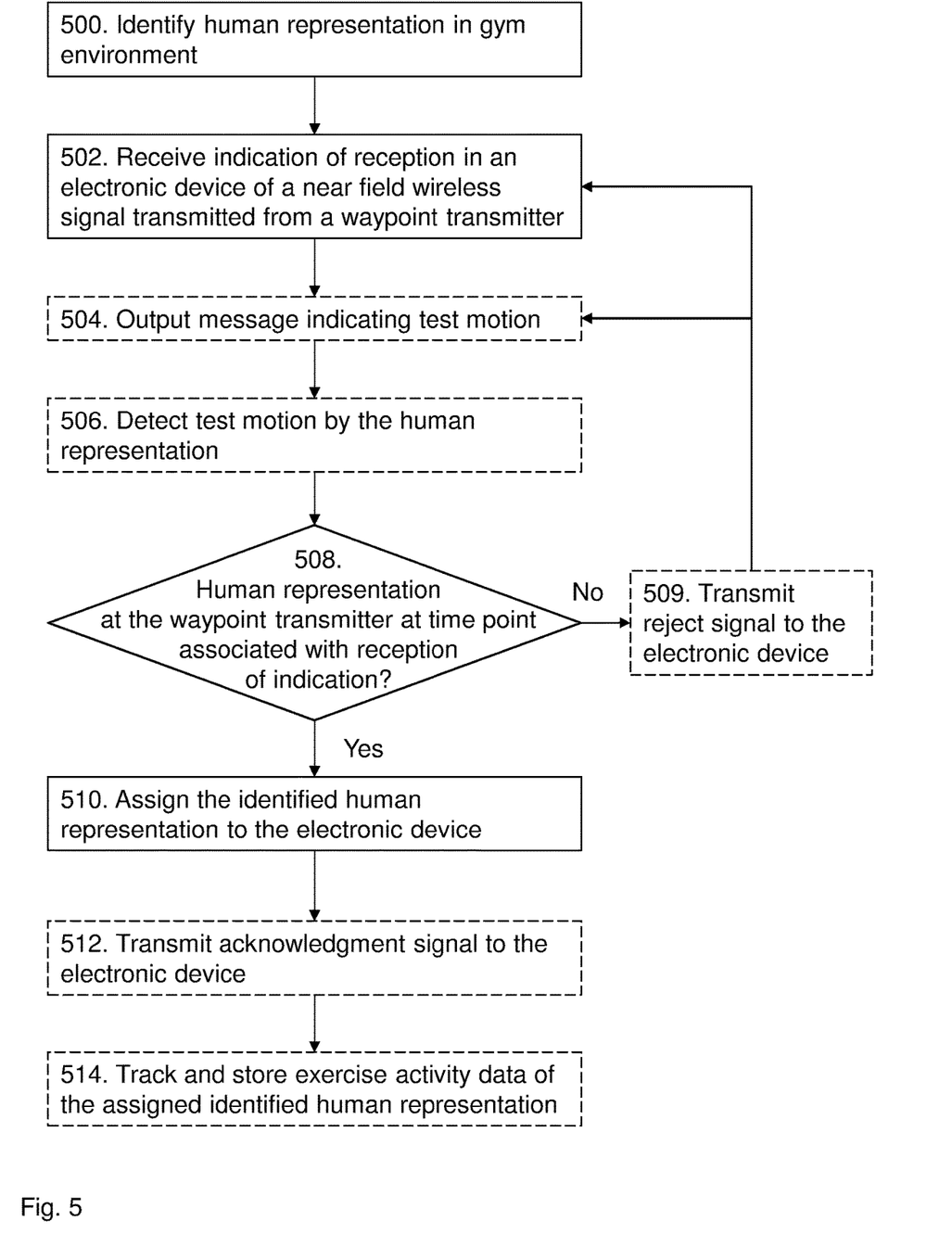
FIG. 5 shows a flowchart comprising various steps included in a method for monitoring activity in a gym environment according to various embodiments of the proposed solution.

FIG. 5 shows a flow chart of various steps included in different embodiments of a method carried out in accordance with the proposed solution.

In step 500, at least one human representation O1 is identified in the gym environment 100. After identification of an object as the human representation O1, the monitoring system 1 is configured to track movement of the human representation. It may be noted that the proposed solution is adapted to operate also when a plurality of human representations O1, O2, O3 are identified and tracked in the gym environment 100.

In step 502, an indication is obtained in the system 200, identifying reception in an electronic device 11 of a near field wireless signal 41 transmitted from a waypoint transmitter 40 arranged at a predetermined location 45 in the gym environment.

It may be noted that steps 500 and 502 may be carried out in any order. In other words, the system 200 may be configured to start identification and tracking of a human representation after, and even in response to, receiving the indication of reception of a near field wireless signal 41 in the electronic device 11.

In various embodiments, the indication of reception of a near field wireless signal 41 in the electronic device 11 is a message received in the system 200, such as by the transceiver 60, from the electronic device 11. Said message may thus constitute a request to assign a human representation to the electronic device 11, for tracking of exercise data to a person or account associated with the electronic device 11.

In step 504, which may be included in some embodiments, the system 200 outputs a message indicating a test motion, for the person carrying the electronic device 11 to carry out.

In step 506, which may be included if step 504 is included, the system 200 is configured to detect, using the monitoring system 1, whether a movement of the identified human representation corresponding to said test motion is carried out.

In step 508, it is determined whether there is a human representation present at the waypoint transmitter 40 at time point associated with reception of indication. If this is the case, and potentially also the validation using a test motion is affirmed, it be determined whether successful or failed assignment of the identified human representation O1 to said electronic device 11 is obtained.

In step 510, responsive to detecting presence of the identified human representation at the location 45 at a point in time associated with the reception in the electronic device of the near field wireless signal 41, the identified human representation O1 is assigned to said electronic device 11. Thereby, the system 200 has appropriately established a linked connection between the electronic device 11 and the identified human representation O1 such that, going forward, exercise activity determined to be carried out based on detected movement of the human representation O1 in the gym environment is stored or otherwise associated with the electronic device 11.

Where the additional steps 504 and 506 are carried out, the assigning of the identified human representation O1 to the electronic device 11 is carried out responsive to positive detection of movement of the identified human representation O1 corresponding to said test motion.

In step 509, if the connection fails, i.e. the system 200 fails to clearly establish that a human representation was present at the waypoint transmitter upon the electronic device 11 receiving the nearfield signal 41, the system 200 may output a signal or message indicating rejection. The process may then be routed back to wait for a new indication of the nearfield signal 45 being received in the electronic device 11, i.e. after a new attempt to tap or approach the waypoint transmitter 40 made by the person carrying the electronic device 11. Alternatively, the process will route to the step 504 of outputting a message indicating a test motion. Where step 504 has already been carried out at least once, a different test motion may be indicated the second time step 504 is carried out. In some embodiments, steps 504 and 506 are only implemented after failed connection at step 508, i.e. not automatically after step 502.

In step 512, upon successful association of the human representation O1 and the electronic device 11, an acknowledgment message or signal is output by the system for detection by the person carrying the electronic device 11. As noted, this may be provided through the electronic device 11, or by a separate output interface at the waypoint transmitter 40.

In step 514, the system 200 proceeds to store exercise activity data such that it is associated with said electronic device 11, based on movement detected by the monitoring system 1 of the assigned identified human representation O1.

The method described with reference to FIG. 5 may terminate once the identified human representation O1 exits the gym environment 100, or by the receiving a termination signal from the electronic device 11.

Further features and characteristics of the method may further include any of the specific solutions presented herein.

In the following, a set of items are recited to summarize some aspects and embodiments of the invention as disclosed in the foregoing.

Item 1: A system (200) for monitoring activity in a gym environment (100), wherein the system comprises:
  a monitoring system (1) configured to identify human representations in the gym environment and track movement of the human representations;
  a transceiver unit (60) for receiving communication signals within the gym environment;
  a waypoint transmitter (40) arranged at a predetermined location (45) in the gym environment and configured to transmit a near field wireless signal (41);
  a control system (50) configured to assign a specific human representation (O1) to an electronic device (11), responsive to the monitoring system detecting presence of the specific human representation at said location at a point in time associated with reception in the electronic device of the near field wireless signal.

Item 2: The system of item 1, wherein the control system is configured to store exercise activity data associated with said electronic device, based on movement detected by the monitoring system of the assigned specific human representation.

Item 3: The system of item 1 or 2, further being configured to output a message indicating a test motion, wherein the control system is configured to assign the specific human representation to said electronic device based on the monitoring system detecting a movement of the specific human representation corresponding to said test motion.

Item 4: The system of item 3, wherein the control system is configured to control the transceiver unit to transmit said message to the electronic device.

Item 5: The system of item 3, wherein the control system is configured to output said message on an interface arranged at said location.

Item 6: The system of any of items 3-5, wherein the control system is configured to assign the specific human representation to said electronic device based on the monitoring system detecting the movement corresponding to said test motion within a predetermined time period.

Item 7. The system of any of items 3-6, wherein said test motion is randomly selected from a group of test motions.

Item 8. The system of any preceding item, further being configured to determine a physical characteristic of the specific human representation, and to assign the specific human characteristic to said electronic device based on the determined physical characteristic matching prestored characteristic data associated with said electronic device.

Item 9. The system of any preceding item, wherein the control system is configured to control the transceiver unit to transmit an acknowledgment signal (130) to the electronic device, responsive to successful assignment of the specific human representation to said electronic device.

Item 10. The system of any preceding item, wherein the monitoring system comprises:
  a plurality of cameras (2) having overlapping fields of view, and
  logic (3,4) configured to process video streams from the plurality of cameras for detection of key points of an object, and to associate said key points to positions on a human body.

Item 11. The system of any preceding item, wherein the control system is configured to determine the point in time associated with reception based on a wireless communication signal (120) received in the transceiver unit from the electronic device.

Item 12. A method for monitoring activity in a gym environment, the method comprising:
  identifying (500) a human representation in the gym environment and tracking movement of the human representation, using a monitoring system;
  receiving (502) an indication of reception in an electronic device of a near field wireless signal transmitted from a waypoint transmitter arranged at a predetermined location in the gym environment;
  assigning (510) the identified human representation to said electronic device, responsive to detecting presence of the identified human representation at said location at a point in time associated with the reception in the electronic device of the near field wireless signal.

Item 13. The method of item 12, comprising:
  storing (514) exercise activity data associated with said electronic device, based on movement detected by the monitoring system of the assigned identified human representation.

Item 14. The method of item 12 or 13, comprising:
  outputting (504) a message indicating a test motion, wherein the assigning of the identified human representation to said electronic device is carried out based on detecting (506) a movement of the identified human representation corresponding to said test motion.

Item 15. The method of item 14, wherein the message is transmitted to the electronic device for output on the electronic device.

Item 16. The method of item 15, wherein the message is output on an interface arranged at said location.

Item 17. The method of any of items 14-16, wherein the assigning is carried out based on detecting the movement corresponding to said test motion within a predetermined time period.

Item 18. The method any of items 14-17, comprising: randomly selecting said test motion from a group of test motions.

Item 19. The method of any of items 14-19, further comprising:
determining a physical characteristic of the identified human representation, wherein the assigning is carried out based on the determined physical characteristic matching prestored characteristic data associated with said electronic device.

Item 20. The method of any of items 12-19, comprising: transmitting (512) an acknowledgment signal to the electronic device, responsive to successful assignment of the identified human representation to said electronic device.

Item 21. The method of any of items 12-20, wherein the identifying (500) comprises:
capturing video streams from a plurality of cameras having overlapping fields of view, and
processing the video streams for detection of key points of an object and associating said key points to positions on a human body.

Item 22. The method of any of items 12-21, comprising: determining the time point associated with reception (502) based on a wireless communication signal (120) received from the electronic device.

What is claimed is:

1. A system for monitoring activity in a gym environment, wherein the system comprises:
   a monitoring system configured to identify one or more human representations in the gym environment and track movement of the one or more human representations, wherein the monitoring system includes:
      a plurality of cameras having overlapping fields of view, and
      logic configured to process video streams from the plurality of cameras for detection of key points of an object, and to associate said key points to positions on a human body;
   a transceiver unit for receiving communication signals from a plurality of electronic devices within the gym environment;
   a waypoint transmitter arranged at a predetermined location in the gym environment and configured to transmit a near field wireless signal detectable by the plurality of electronic devices;
   a control system configured to:
      assign a specific human representation of the one or more human representations to a specific electronic device of the plurality of electronic devices, responsive to the monitoring system detecting presence of the specific human representation at the predetermined location at a point in time associated with reception in the specific electronic device of the near field wireless signal, wherein the specific electronic device is associated with a user corresponding to the specific human representation; and
      store exercise activity data associated with the specific electronic device, wherein the exercise data is based on movement detected by the monitoring system of the specific human representation assigned to the specific electronic device.

2. The system of claim 1, further being configured to output a message indicating a test motion, wherein the control system is configured to assign the specific human representation to the specific electronic device based on the monitoring system detecting a movement of the specific human representation corresponding to said test motion.

3. The system of claim 2, wherein the control system is configured to control the transceiver unit to transmit said message to the specific electronic device.

4. The system of claim 2, wherein the control system is configured to output said message on an interface arranged at the predetermined location.

5. The system of claim 2, wherein the control system is configured to assign the specific human representation to the specific electronic device based on the monitoring system detecting the movement corresponding to said test motion within a predetermined time period.

6. The system of claim 2, wherein said test motion is randomly selected from a group of test motions.

7. The system of claim 1, further being configured to determine a physical characteristic of the specific human representation, and to assign the specific human characteristic to the specific electronic device based on the determined physical characteristic matching prestored characteristic data associated with the specific electronic device.

8. The system of claim 1, wherein the control system is configured to control the transceiver unit to transmit an acknowledgment signal to the specific electronic device, responsive to successful assignment of the specific human representation to the specific electronic device.

9. The system of claim 1, wherein the control system is configured to determine the point in time associated with reception based on a wireless communication signal received in the transceiver unit from the specific electronic device.

10. A method for monitoring activity in a gym environment, the method comprising:
   identifying a human representation in the gym environment and tracking movement of the human representation, using a monitoring system having a plurality of cameras having overlapping fields of view, and logic configured to process video streams from the plurality of cameras for detection of key points of an object, and to associate said key points to positions on a human body;
   receiving an indication of reception in an electronic device associated with a user of a near field wireless signal transmitted from a waypoint transmitter arranged at a predetermined location in the gym environment;
   assigning the identified human representation to the electronic device associated with the user, responsive to detecting presence of the identified human representation at said location at a point in time associated with the reception in the electronic device of the near field wireless signal, wherein the user corresponds to the identified human representation; and
   storing exercise activity data associated with the electronic device, wherein the exercise activity data is based on movement detected by the monitoring system of the identified human representation assigned to the electronic device.

11. The method of claim 10, comprising:
  outputting a message indicating a test motion, wherein the assigning of the identified human representation to the electronic device is carried out based on detecting a movement of the identified human representation corresponding to said test motion.

12. The method of claim 11, wherein the message is transmitted to the electronic device for output on the electronic device.

13. The method of claim 12, wherein the message is output on an interface arranged at the predetermined location.

14. The method of claim 11, wherein the assigning is carried out based on detecting the movement corresponding to said test motion within a predetermined time period.

15. The method of claim 11, comprising:
  randomly selecting said test motion from a group of test motions.

16. The method of claim 11, further comprising:
  determining a physical characteristic of the identified human representation, wherein the assigning is carried out based on the determined physical characteristic matching prestored characteristic data associated with the electronic device.

17. The method of claim 10, comprising:
  transmitting an acknowledgment signal to the electronic device, responsive to successful assignment of the identified human representation to the electronic device.

* * * * *